(12) United States Patent
Midgett et al.

(10) Patent No.: US 11,426,590 B2
(45) Date of Patent: Aug. 30, 2022

(54) LEADLESS CARDIAC PACEMAKER DEVICE CONFIGURED TO PROVIDE INTRA-CARDIAC PACING

(71) Applicant: BIOTRONIK SE & Co. KG, Berlin (DE)

(72) Inventors: Madeline Anne Midgett, Portland, OR (US); R. Hollis Whittington, Portland, OR (US); Ravi Kiran Kondama Reddy, Portland, OR (US); Christopher Jones, Oregon City, OR (US); Shayan Guhaniyogi, Portland, OR (US); Dirk Muessig, West Linn, OR (US); Larry Stotts, Tigard, OR (US)

(73) Assignee: BIOTRONIK SE & Co. KG, Berlin (DE)

( * ) Notice: Subject to any disclaimer, the term of this patent is extended or adjusted under 35 U.S.C. 154(b) by 22 days.

(21) Appl. No.: 16/905,134

(22) Filed: Jun. 18, 2020

(65) Prior Publication Data
US 2021/0060346 A1   Mar. 4, 2021

Related U.S. Application Data

(60) Provisional application No. 62/895,510, filed on Sep. 4, 2019.

(51) Int. Cl.
*A61N 1/05*   (2006.01)
*A61N 1/365*  (2006.01)
*A61N 1/375*  (2006.01)

(52) U.S. Cl.
CPC ....... *A61N 1/36585* (2013.01); *A61N 1/0565* (2013.01); *A61N 1/36542* (2013.01);
(Continued)

(58) Field of Classification Search
None
See application file for complete search history.

(56) References Cited

U.S. PATENT DOCUMENTS 9,492,668 B2   11/2016   Sheldon et al.
9,492,669 B2   11/2016   Demmer et al.
(Continued)

FOREIGN PATENT DOCUMENTS

EP   3218049 B1   4/2018

*Primary Examiner* — Brian T Gedeon
(74) *Attorney, Agent, or Firm* — Laurence A. Greenberg; Werner H. Stemer; Ralph E. Locher

(57) ABSTRACT

A leadless pacemaker device for providing an intra-cardiac pacing includes processing circuitry configured to generate ventricular pacing signals for stimulating ventricular activity at a ventricular pacing rate, a first sensor configuration receiving a first sense signal, and a second sensor configuration receiving a second sense signal. The processing circuitry derives, in a first sensing state, atrial events from the first sense signal for controlling the ventricular pacing rate based on the atrial events. The processing circuitry switches, based on at least one switching criterion, from the first sensing state to a second sensing state in which the processing circuitry derives atrial events from the second sense signal. The second sense signal is received by the second sensor configuration for detection of atrial events and the second sensor configuration is a motion sensor or a sound sensor. A method for operating the pacemaker device is also provided.

13 Claims, 6 Drawing Sheets

(52) U.S. Cl.
CPC ....... *A61N 1/36564* (2013.01); *A61N 1/3756* (2013.01); *A61N 1/37512* (2017.08); *A61N 1/057* (2013.01); *A61N 1/37518* (2017.08)

(56) References Cited

U.S. PATENT DOCUMENTS

| | | |
|---|---|---|
| 9,724,519 B2 | 8/2017 | Demmer et al. |
| 9,808,628 B2 | 11/2017 | Sheldon et al. |
| 2013/0138006 A1 | 5/2013 | Bornzin et al. |
| 2016/0023000 A1 | 1/2016 | Cho et al. |
| 2016/0129262 A1* | 5/2016 | Sheldon ............... A61N 1/3756 607/17 |
| 2018/0021581 A1 | 1/2018 | An et al. |
| 2018/0028814 A1 | 2/2018 | Ghosh |
| 2018/0117338 A1* | 5/2018 | Kane .................... A61B 5/1118 |
| 2018/0161580 A1* | 6/2018 | Demmer ............ A61N 1/36585 |
| 2019/0168008 A1 | 6/2019 | Maile et al. |

\* cited by examiner

LEADLESS CARDIAC PACEMAKER DEVICE CONFIGURED TO PROVIDE INTRA-CARDIAC PACING

CROSS-REFERENCE TO RELATED APPLICATION

This application claims the benefit, under 35 U.S.C. § 119(e), of U.S. Provisional Patent Application No. 62/895,510, filed Sep. 4, 2019; the prior application is herewith incorporated by reference in its entirety.

BACKGROUND OF THE INVENTION

Field of the Invention

The present invention generally relates to a leadless cardiac pacemaker device for providing an intra-cardiac pacing, in particular a ventricular pacing.

Leadless pacemakers, in contrast to pacemakers implanted subcutaneously using leads extending transvenously into the heart, avoid leads in that the pacemaker device itself is implanted into the heart, the pacemaker having the shape of a capsule for implantation into cardiac tissue, in particular the right ventricular wall of the right ventricle. Such leadless pacemakers exhibit the inherent advantage of not using leads, which can reduce risks for the patient involved with leads transvenously accessing the heart, such as the risk of pneumothorax, lead dislodgement, cardiac perforation, venous thrombosis and the like.

Leadless pacemakers may specifically be constructed for implantation in the right ventricle and, in this case, during implant are placed in or on the right ventricular wall. Ventricular pacing may for example be indicated in case a dysfunction at the AV node occurs, but the sinus node function is intact and appropriate. In such a case in particular a so-called VDD pacing may be desired, involving ventricular pacing with atrial tracking and hence requiring a sensing of atrial activity in order to pace at the ventricle based on intrinsic atrial contractions.

Pacing using atrial tracking is in particular motivated by patient hemodynamic benefits of atrioventricular (AV) synchrony by utilizing an appropriate sinus node function to trigger ventricular pacing, potentially allowing to maximize ventricular preload, to limit AV valve regurgitation, to maintain low mean atrial pressure, and to regulate autonomic and neurohumoral reflexes.

Publications have explored solutions to use modalities to detect mechanical events of atrial contractions, including the sensing of motion, sound and pressure. For example, U.S. Patent Application Publication No. 2018/0021581 A1 discloses a leadless cardiac pacemaker including a pressure sensor and/or an accelerometer to determine an atrial contraction timing. As mechanical events generally exhibit a small signal volume, signal detection based on mechanical events, for example motion, sound or pressure, may be difficult to sense, in particular when the leadless pacemaker device is placed in the ventricle and hence rather far removed from the atrium of which contractions shall be sensed. In addition, wall motion and movement of blood generated by atrial contractions may not be directly translated to the ventricle, and cardiac hemodynamic signals, such as motion, heart sounds and pressure, are likely affected by external factors such as posture and patient activity.

European Patent EP 3 218 049 B1, corresponding to U.S. Pat. Nos. 9,808,628; 9,724,519; 9,492,669; and 9,492,668, describes a leadless pacemaker device that is configured for implantation in a ventricle of a heart of a patient and is configured to switch from an atrioventricular synchronous pacing mode to an asynchronous pacing mode in response to detection of one or more ventricular undersensing events.

U.S. Patent Application Publication No. 2018/0028814 A1 discloses an implantable medical device system operating in an atrial synchronized ventricular pacing mode and switching to an atrial asynchronous pacing mode when pacing mode switching criteria are met. A control circuit of the system detects a cycle length change between two atrial cycle lengths determined from a cardiac signal that includes far-field atrial triggering events. If the cycle length change is greater than a change threshold, the control circuit determines if the pacing mode switching criteria are satisfied subsequent to detecting the cycle length change.

Signals relating to an atrial activity are inherently small when received in the ventricle. This applies both to electrical signals received by using a suitable electrode configuration of the leadless pacemaker device and to mechanical signals such as motion signals, pressure signals or sound signals. Considering the limitations to the reception of electrical and mechanical signals, it is challenging to provide for a reliable atrial tracking to control a ventricular pacing rate.

SUMMARY OF THE INVENTION

It is accordingly an object of the invention to provide a leadless pacemaker device and a method for operating a leadless pacemaker device, which overcome the hereinafore-mentioned disadvantages of the heretofore-known devices and methods of this general type and which allow, in particular, for a reliable detection of signals relating to an atrial activity and the use of such signals for controlling a ventricular pacing rate for a ventricular pacing.

With the foregoing and other objects in view there is provided, in accordance with one aspect of the invention, a leadless cardiac pacemaker device configured to provide for an intra-cardiac pacing, the leadless pacemaker device comprising a processing circuitry configured to generate ventricular pacing signals for stimulating ventricular activity at a ventricular pacing rate, a first sensor configuration configured to receive a first sense signal, and a second sensor configuration configured to receive a second sense signal. In this case, the processing circuitry is configured to derive, in a first sensing state, atrial events from the first sense signal for controlling the ventricular pacing rate based on the atrial events, and the processing circuitry is further configured to switch, based on at least one switching criterion, from the first sensing state to a second sensing state in which the processing circuitry is configured to derive atrial events from the second sense signal.

The leadless pacemaker device includes multiple sensor configurations. The multiple sensor configurations herein serve to detect different sense signals. In one embodiment, the different sensor configurations employ different physical detection mechanisms, such as an electrical sensing of electrical signals or a mechanical sensing of mechanical signals having a mechanical origin. As the sensor configurations employ different sensing mechanisms, the sensor configurations output different signals having a different nature and different characteristics, wherein under certain conditions atrial events may be detected in one signal and under other conditions in another signal.

Hence, it is proposed to switch between different sensing states in order to detect atrial events. In a first sensing state the processing circuitry is configured to identify atrial events from the first sense signal for controlling the ventricular pacing rate based on the atrial events. By applying one or multiple switching criteria, the processing circuitry may switch from the first sensing state to another, second sensing state in which atrial events are derived from the second sensor signal obtained with the second sensor configuration in order to then control the ventricular pacing rate based on the atrial events detected in the second sense signal. Hence, if for example the first sense signal becomes weak and does not allow any longer for a reliable detection of atrial events, the processing circuitry may switch from the first sensing state to the second sensing state in order to use the second sensor configuration to receive a second sense signal and to derive atrial events from the second sense signal.

When the processing circuitry is in the first sensing state, the second sensor configuration and a corresponding sensing circuitry may be switched off in order to save power, such that signals are received only by using the first sensor configuration. If, in turn, the processing circuitry is in the second sensing state, the first sensor configuration and a corresponding sensing circuitry may be switched off, such that signals are received only by using the second sensor configuration.

One sensor configuration may be assumed as a master or primary sensor, whereas the other sensor configuration is assumed as slave or secondary sensor. In a default state, for example at startup or in case both sense signals in principle are suited for controlling a ventricular pacing, the processing circuitry is in the first sensing state and hence uses the first sensor configuration for detecting atrial events and to control a ventricular pacing rate based on such atrial events. Hence, as long as the first sense signal allows for a reliable detection of atrial events and a stable control of a ventricular pacing operation, the processing circuitry remains in the first sensing state and uses the first electrode configuration for an atrial tracking. Only if, according to certain switching criteria, it is found that the first sense signal no longer is usable for a reliable detection of atrial events, a switching from the first sensing state to the second sensing state is initiated in order to detect atrial events in the second sensing state by making use of the second sensor configuration and signals received by using the second sensor configuration.

The leadless pacemaker device hence uses multiple sensor configurations to provide for a redundancy in the reception of signals indicative of atrial events. If one sensor configuration no longer provides for signals suitable for deriving information with respect to an intrinsic atrial rate, the device may switch to another sensing state in order to use another sensor configuration for detecting other signals and for deriving atrial events based on such other signal.

The leadless pacemaker device may include more than two sensor configurations, for example three, four or five sensor configurations using sensors of different physical principles and hence receiving electrical signals and/or mechanical signals, such as pressure signals, motion signals or sound signals. The processing circuitry, in this case, may be configured to switch between more than two sensing states, such that the processing circuitry may switch from one sensor configuration to the other to evaluate whether atrial events can be derived reliably from a respective sense signal.

In one embodiment, one of the first sensor configuration or the second sensor configuration includes at least two electrodes for receiving an electrical sense signal indicative of an atrial activity. In this case, one of the sensor configurations is configured to receive electrical signals in the far field, wherein the two electrodes beneficially are located as far as possible from each other in order to allow for a reliable detection of a differential signal in between the two electrodes relating to electrical activity in the atrium.

The first or the second sensor configuration may be configured for electrical sensing using electrodes. An electrical sensor may hence be used as primary sensor for a sensing in the first sensing state or as secondary sensor for a sensing in the second sensing state, wherein the selection may be set in the device by default or may be determined during initial set up based on for example specific conditions of a patient, such as an implant location, an activity lifestyle, a cardiac rhythm or the like.

The leadless pacemaker device may for example include a housing and an configuration of electrodes disposed on the housing for emitting pacing signals and, in addition, for receiving reception signals. The housing provides for an encapsulation of the leadless pacemaker device, the leadless pacemaker device including all required components for autarkic operation, such as the processing circuitry, an energy storage such as a battery, electric and electronic circuitry and the like, within the housing. The housing is fluid-tight such that the leadless pacemaker device may be implanted into cardiac tissue and may be kept in cardiac tissue over an extended period of time to provide for a long-term, continuous cardiac pacing operation.

In one aspect, the electrode configuration includes a first electrode disposed in the vicinity of a tip of the housing. The first electrode shall come to rest on cardiac tissue in an implanted state of the pacemaker device, such that the first electrode contacts cardiac tissue at a location effective for injecting a stimulating signal into cardiac tissue for provoking a pacing action, in particular a ventricular pacing.

In one aspect, the electrode configuration includes a second electrode formed for example by an electrode ring circumferentially extending about the housing. Alternatively, the second electrode may for example be formed by a patch or another electrically conductive area formed on the housing. The second electrode is placed at a distance from the tip of the housing and hence at a distance from the first electrode disposed at the tip.

In one embodiment, the housing includes a far end opposite the tip, the electrode configuration including a third electrode disposed on the housing at the far end opposite the tip. The third electrode is operatively connected to the processing circuitry, such that the processing circuitry is enabled to receive and process signals received via the third electrode. The third electrode may be formed as a ring electrode which surrounds the housing at the far end.

In one aspect, the processing circuitry is configured to process, as a reception signal indicative of atrial activity, a sense signal between the first or the second electrode and the third electrode. Such signal vector arising between the first or second electrode and the third electrode may be referred to as far-field vector, the first or second electrode and the third electrode exhibiting a rather large distance with respect to each other such that a far-field differential signal may be picked up at a reasonable signal-to-noise ratio.

Electrical sensing may be performed by all electrode vector combinations, including both atrial and ventricular vectors using the same electrode pair or different electrode pairs. In one embodiment, a single electrode pair (e.g. first electrode and second electrode; first electrode and third electrode; or second electrode and third electrode) may be used for sensing both atrial (far-field) and ventricular (near-field) signals.

In one aspect, another one of the first sensor configuration or the second sensor configuration includes at least one of a motion sensor for sensing a movement signal, a pressure sensor for sensing a pressure signal, and a sound sensor for sensing a sound signal. The other of the first sensor configuration and the second sensor configuration hence provides for a sensing making use of a different sensing technology in particular to sense signals having a mechanical origin in the atrium.

A motion sensor, in one embodiment, may in particular include an accelerometer configured to sense an acceleration. The accelerometer herein may sense an acceleration along one axis or along multiple axes, for example along all three spatial directions. If the accelerometer allows for a sensing of acceleration along three axes, a single axis may be selected for sensing by a default setting or based on an evaluation which axis is the best for sensing upon a tracking initiation. Alternatively, the selection of a single axis for sensing may be adapted based on changing conditions. Yet alternatively, two or three axes may be used for sensing in order to provide for a multi-dimensional sensing of motion.

If the sensor configuration includes a pressure sensor, the pressure sensor may be located in a housing of the leadless pacemaker device, wherein a window on the housing may allow for a direct measurement of pressure in the vicinity of the leadless pacemaker device. Alternatively, the pressure sensor may for example be embodied by a piezo element coupled to the housing (made for example of metal), having the advantage that no window interrupting the hermetic enclosure of the housing is required to provide for a pressure sensing.

A sound sensor may for example include a microphone allowing for a detection of sound generated by the motion of the heart, in particular a so-called fourth heart sound (S4) also known as the atrial gallop occurring when the atria contract to force blood into the ventricles.

In one aspect, the processing circuitry is configured to detect, in the first sensing state, an atrial event from the first sense signal in a first search window having a predefined temporal position with respect to a ventricular event caused by a ventricular activity. Hence, in the first sensing state the first sense signal is used to search for atrial events in a predefined search window, wherein the first sense signal may be blanked outside of the search window such that signal portions relating to a heart activity other than an atrial activity are suppressed. Because the search is limited to a predefined window, which is timed based on an expected time of occurrence of an atrial event following a prior ventricular event, power may be saved as a sensing channel and a corresponding circuitry is not powered continuously, but only in certain phases in which atrial events are expected to occur.

Likewise, the processing circuitry may be configured to detect, in the second sensing state, an atrial event from the second sense signal in a second search window having a predefined second temporal position with respect to a ventricular event caused by a ventricular activity. A detection of atrial events based on the second sense signal hence also takes place by using a search window in which an atrial event is predicted to occur.

The first search window and the second search window herein may have the same temporal width and the same time delay with respect to a prior ventricular event. The first search window and the second search window, in another embodiment, however may have a different temporal width and/or a different temporal position with respect to a prior ventricular event. The configuration of the search window may take account of the physical nature of a sense signal used in a particular sensing state, based on the fact that for example electrical signals may travel faster than mechanical signals, such as motion signals, pressure signals and sound signals. A search window related to the detection of atrial events in a sense signal received by using a sensor for detecting signals of mechanical origin, such as an accelerometer, a pressure sensor or a sound sensor, hence may be configured differently than a search window related to the detection of atrial events in an electrical sense signal.

Atrial events in each sense signal may be identified based on a processing involving for example a filtering, such as a bandpass filtering, and/or a rectification. A threshold crossing technique by monitoring whether a processed signal crosses a predefined, potentially adaptive threshold may be employed to identify an atrial event in a signal.

In one embodiment, the processing circuitry is configured to analyze, as a switching criterion, whether an atrial event is detectable in the first sense signal, wherein the processing circuitry is configured to switch to the second sensing state if atrial events are not detectable in at least a portion of a predetermined number of heart cycles. The processing circuitry hence evaluates whether atrial signals are detectable at all in the first sense signal. If atrial events are not detectable in the first sense signal for a predefined number of heart cycles, such as 5 or 10 heart cycles, or if atrial events are not detectable in a certain percentage, such as 50%, of a preset number of heart cycles, the processing circuitry may initiate a switching from the first sensing state to the second sensing state in order to then use the second sensor configuration and the second sense signal received by using the second sensor configuration for a detection of atrial events.

In another approach, the processing circuitry may be configured to analyze, as a switching criterion, at least one characteristic value derived from the first sense signal, wherein the processing circuitry may be configured to switch to the second sensing state based on the analysis of the at least one characteristic value. As characteristic values in particular a positive and/or negative peak value, a positive and/or negative average value, a peak width and a frequency content in the first signal may be computed. The characteristic value herein may in particular be determined in a specified search window, such that the peak value for example relates to a peak in a signal due to an atrial activity. A positive average value may relate to the average of signal portions above a baseline, whereas a negative average value may relate to the average of signal portions below a baseline of the signal. The peak width may be determined as a full-width-at-half-maximum (FWHM). The determination of a frequency content may involve a bandpass filtering and to compute an energy content in a certain frequency band of the signal.

The characteristic value determined from the sensor signal may be analyzed for example with respect to a trend over multiple heart cycles in order to determine whether a potential risk is present that atrial events are no longer detectable. Hence, if it is for example found that the (positive or negative) peak amplitude has a decreasing trend and may in particular approach a threshold used for the identification of an atrial event, it may be concluded that the first sense signal received by using the first sensor configuration may no longer be suitable for an atrial tracking, such that the processing circuitry may switch to the second sensing state.

Additionally or alternatively, the characteristic value may be analyzed to determine whether an actual characteristic value falls within a predefined distance from a threshold value. If it is found that a characteristic value, for example a positive or negative peak value, is close to a threshold, a switching from the first sensing state to the second sensing state may be initiated.

The switching according to an analysis of characteristic values of the sense signal has the inherent advantage that a switching to another sensing state may take place prior to actually losing any atrial events, hence prior to let heart cycles pass without detecting an atrial event.

In one aspect, the processing circuitry is configured to switch from the second sensing state to the first sensing state in case atrial events adequate for a pacing are again detectable in the first sense signal. The processing circuitry hence is configured to automatically switch back to the first sensing state if it is evaluated that the first sensor configuration again allows for a stable detection of an atrial rate. For this, the first sensor configuration may continuously or in certain intervals be used to receive and process sense signals in order to evaluate whether a switching back to the first sensing state may be appropriate.

In another aspect, the processing circuitry may be configured to switch to an asynchronous pacing mode in case atrial events adequate for a pacing are not detectable in the first sensing state and the second sensing state. When the processing circuitry is in the first sensing state or the second sensing state, atrial events are detected by using the respective sensor configuration, and an atrial tracking is enabled in order to control a ventricular pacing rate, i.e., a timing of ventricular pacing signals to be generated and injected into the ventricle at the implant location of the leadless pacemaker device. The pacemaker device hence is in a synchronous pacing mode, inducing a pacing in the ventricle in synchrony with an atrial rate. If however neither the first sense signal nor the second sense signal allow for a reliable detection of atrial events, no synchronous pacing in the ventricle is possible, such that the pacemaker device switches to an asynchronous pacing mode in which the ventricular pacing rate may for example be controlled according to a rate response mechanism in which the pacing rate is varied according to signals indicative of a physical constitution and activity of a patient. For example, during inactive phases the pacing rate may be reduced, whereas in times of heavy activity of the patient the pacing rate may be increased.

When in the asynchronous pacing mode, the processing circuitry may continuously monitor the sensor signals of the first sensor configuration, or the first sensor configuration and the second sensor configuration. If the sense signal of the first sensor configuration again allows for a stable detection of atrial events adequate for a pacing, the processing circuitry may switch back to the first sensing state. If the sense signal of the second sensor configuration allows for a stable detection of atrial events, the processing circuitry instead may switch to the second sensing state.

The leadless pacemaker device may provide for a continuous ventricular pacing at an adaptive ventricular pacing rate. In another embodiment, the leadless pacemaker device may be configured to provide a pacing in the ventricle only if no intrinsic contraction signals in the ventricle at a suitable timing can be detected. Hence, in one embodiment, the processing circuitry is configured to generate a ventricular pacing signal if no intrinsic ventricular sense signal is detected within a predefined time window following a prior ventricular event. If, instead, an intrinsic ventricular sense signal—over one or multiple cycles—is detected within the predefined time window following the prior ventricular event, no pacing signal is generated and injected, such that in that case no pacing action takes place, but the pacemaker device is in an intrinsic conduction mode without providing an artificial pacing.

With the objects of the invention in view, there is also provided a method for operating a leadless pacemaker device configured to provide for an intra-cardiac pacing, the method comprising: generating, using a processing circuitry, ventricular pacing signals for stimulating ventricular activity at a ventricular pacing rate; receiving, using a first sensor configuration, a first sense signal; deriving, using the processing circuitry, in a first sensing state atrial events from the first sense signal for controlling the ventricular pacing rate based on the atrial events; switching, using the processing circuitry, based on at least one switching criterion from the first sensing state to a second sensing state in which a second sense signal is received using a second sensor configuration; and deriving, using the processing circuitry, atrial events from the second sense signal in the second sensing state.

The advantages and embodiments described above for the leadless pacemaker device equally apply also to the method, such that it shall be referred to the above.

Other features which are considered as characteristic for the invention are set forth in the appended claims.

Although the invention is illustrated and described herein as embodied in a leadless cardiac pacemaker device configured to provide intro-cardiac pacing and a method for operating the leadless cardiac pacemaker device, it is nevertheless not intended to be limited to the details shown, since various modifications and structural changes may be made therein without departing from the spirit of the invention and within the scope and range of equivalents of the claims.

The construction and method of operation of the invention, however, together with additional objects and advantages thereof will be best understood from the following description of specific embodiments when read in connection with the accompanying drawings.

DETAILED DESCRIPTION OF THE INVENTION

Figure 1:
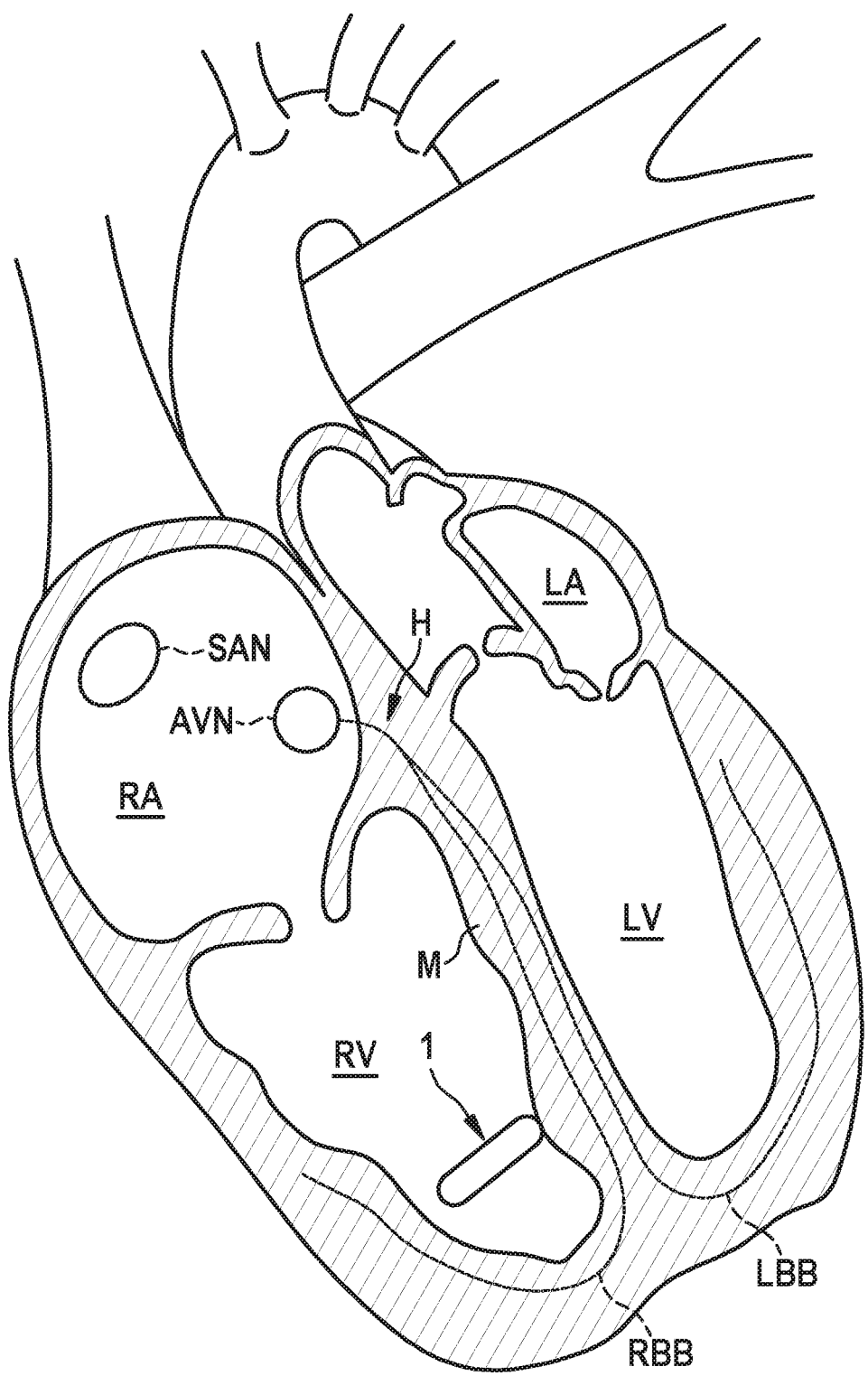
FIG. 1 is a diagrammatic, cross-sectional view of the human heart.

Subsequently, embodiments of the invention shall be described in detail with reference to the drawings. In the drawings, like reference numerals designate like structural elements.

It is to be noted that the embodiments are not limiting for the invention, but merely represent illustrative examples.

In the invention of the instant application it is proposed to provide a leadless pacemaker device providing for an intra-cardiac pacing, in particular a ventricular pacing.

Referring now to the figures of the drawings in detail and first, particularly, to FIG. 1 thereof, there is seen a diagrammatic view of the human heart including the right atrium RA, the right ventricle RV, the left atrium LA and the left ventricle LV, the so-called sinoatrial node SAN being located in the wall of the right atrium RA, the sinoatrial node SAN being formed by a group of cells having the ability to spontaneously produce an electrical impulse that travels through the heart's electrical conduction system, thus causing the heart to contract in order to pump blood through the heart. The atrioventricular node AVN serves to coordinate electrical conduction in between the atria and the ventricles and is located at the lower back section of the intra-atrial septum near the opening of the coronary sinus. From the atrioventricular node AVN the so-called HIS bundle H is extending, the HIS bundle H being formed of heart muscle cells specialized for electrical conduction and forming part of the electrical conduction system for transmitting electrical impulses from the atrioventricular node AVN via the so-called right bundle branch RBB around the right ventricle RV and via the left bundle branch LBB around the left ventricle LV.

In case of a block at the atrioventricular node AVN, the intrinsic electrical conduction system of the heart H may be disrupted, causing a potentially insufficient intrinsic stimulation of ventricular activity, i.e., insufficient or irregular contractions of the right and/or left ventricle RV, LV. In such a case, a pacing of ventricular activity by using a pacemaker device may be indicated, such pacemaker device stimulating ventricular activity by injecting stimulation energy into intra-cardiac tissue, specifically myocardium M.

Within the instant text, it is proposed to use a leadless cardiac pacemaker device 1, as schematically indicated in FIG. 1, for providing for a ventricular pacing action.

Whereas common leadless pacemaker devices are constructed to sense a ventricular activity by receiving electrical signals from the ventricle RV, LV they are placed in, it may be desirable to provide for a pacing action which achieves atrioventricular (AV) synchrony by providing a pacing in the ventricle in synchrony with an intrinsic atrial activity. For such pacing mode, also denoted as atrial tracking, it is required to sense atrial activity and identify atrial events relating to atrial contractions in order to base a ventricular pacing on such atrial events.

Figure 3:
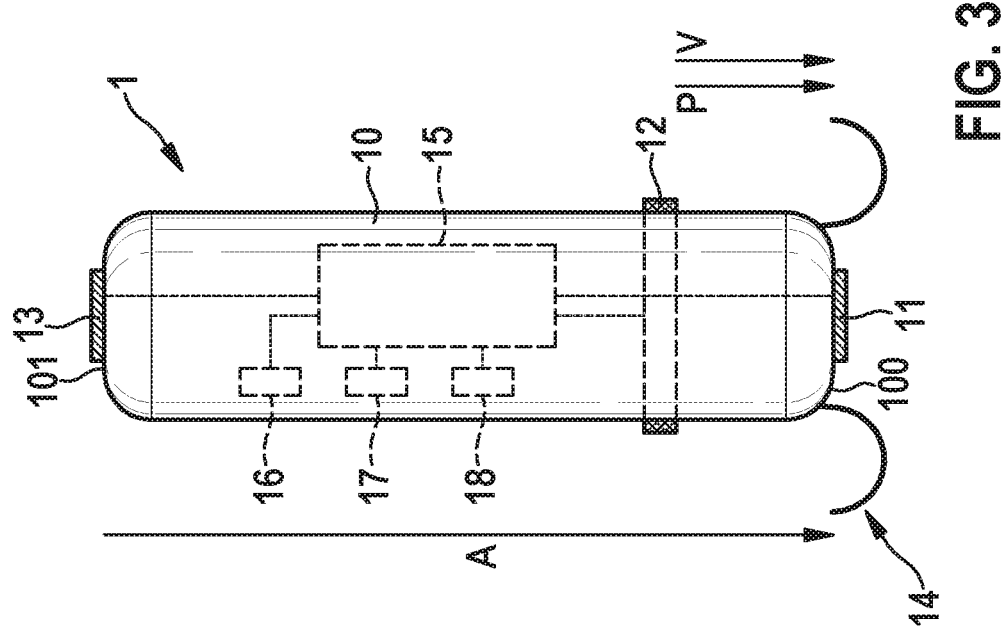
FIG. 3 is an elevational view of a leadless pacemaker device, indicating signal vectors between different electrodes of the leadless pacemaker device.
Figure 2:
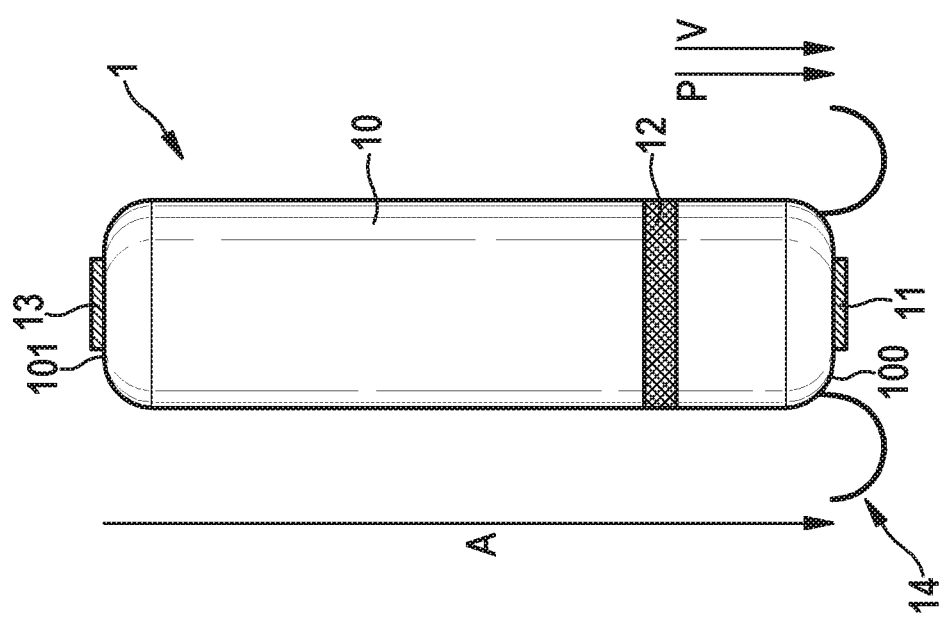
FIG. 2 is an elevational view of a leadless pacemaker device.

Referring now to FIGS. 2 and 3, in one embodiment a leadless pacemaker device 1 configured to provide for an intra-cardiac pacing, in particular employing an atrial tracking, includes a housing 10 enclosing electrical and electronic components for operating the leadless pacemaker device 1. In particular, enclosed within the housing 10 is a processing circuitry 15, including for example also a communication interface for communicating with an external device, such as a programmer wand. In addition, electrical and electronic components such as an energy storage in the shape of a battery are confined in the housing 10. The housing 10 provides for an encapsulation of components received therein, the housing 10 having the shape of, e.g., a cylindrical capsule having a length of for example a few centimeters.

The leadless pacemaker device 1 is to be implanted on intra-cardiac tissue M. For this, the leadless pacemaker device 1 includes, in the region of the tip 100, a fixation device 14 for example in the shape of nitinol wires to engage with intra-cardiac tissue M for fixedly holding the leadless pacemaker device 1 on the tissue in an implanted state.

The leadless pacemaker device 1 does not include leads, but receives signals relating to a cardiac activity, in the illustrated embodiment, by using different sensors located on or in the housing.

In particular, the leadless pacemaker device 1 in the shown embodiment includes an electrode configuration disposed on the housing 10 for receiving electrical signals and also for emitting stimulation signals. In the embodiment of FIGS. 2 and 3, the leadless pacemaker device 1 includes at least two different electrodes 11, 12, 13 making up the electrode configuration and serving to emit pacing signals towards intra-cardiac tissue M for providing a pacing and to sense electrical signals indicative of a cardiac activity, in particular indicative of atrial and ventricular contractions.

A first electrode 11 herein is denoted as a pacing electrode. The first electrode 11 is placed at a tip 100 of the housing 10 and is configured to engage with cardiac tissue M.

A second electrode 12 serves as a counter-electrode for the first electrode 11, a signal vector P arising between the first electrode 11 and the second electrode 12 providing for a pacing vector for emitting pacing signals towards the intra-cardiac tissue M.

In addition, the second electrode 12 may serve as a sensing electrode for sensing signals, in particular relating to ventricular contractions, a signal vector V arising between the second electrode 12 and the first electrode 11, the signal vector V being denoted as near-field vector.

The second electrode 12 is placed at a distance from the first electrode 11 and for example has the shape of a ring extending circumferentially about the housing 10. The second electrode 12 is for example placed at a distance of about 1 cm (or more) from the tip 100 of the housing 10 at which the first electrode 11 is placed.

The leadless pacemaker device 1, in the embodiment of FIGS. 2 and 3, in addition includes a third electrode 13 placed at a far end 101 of the housing 10, the third electrode 13 serving as a sensing electrode to sense signals indicative of cardiac activity in the far-field. The third electrode 13 may be formed as a ring extending circumferentially about the housing. In particular, a signal vector A arises between the third electrode 13 and the first electrode 11, the signal vector A being suited to pick up differential signals indicative for example of atrial contractions and being denoted as far-field vector.

The electrodes 11, 12, 13 are in operative connection with the processing circuitry 15, the processing circuitry 15 being configured to cause the first electrode 11 and the second electrode 12 to emit a pacing signal for providing a stimulation at the ventricle. The processing circuitry 15 furthermore is configured to process signals received via the electrodes 11, 12, 13 to provide for a sensing of cardiac activity, in particular atrial and ventricular contractions.

The electrodes 11, 12, 13 make up a sensor configuration for sensing electrical signals. In particular, the pair of electrodes 11, 13 defining the far-field vector A may allow for a detection of atrial events in an electrical signal received as a differential signal between the electrodes 11, 13.

In one embodiment, the far-field vector A and the near-field vector V may be defined by the same pair of electrodes, and processed separately to enhance different components of the resulting signal.

The leadless pacemaker device 1 in the embodiment of FIGS. 2 and 3 includes further sensors 16, 17, 18, one sensor 16 for example being a motion sensor, in particular an accelerometer, another sensor 17 being a pressure sensor and yet another sensor 18 being a sound sensor. Through the use of such sensors 16, 17, 18 different sense signals may be received in order to allow for an identification of atrial events and other sensor signals, hence improving the detection reliability of atrial events and increasing the stability of an atrial tracking.

Whereas in principle it is possible to operate all sensor configurations 11, 13, 16, 17, 18 continuously in order to receive sensor signals in parallel and to process the sense signals in order to derive atrial events from a combined analysis of the signals, it herein is proposed to provide for a switching between different sensor configurations 11, 13, 16, 17, 18 in order to identify atrial events in a particular sense signal as long as this appears feasible and to switch to another sensing state in case atrial events can no longer be reliably detected in that sense signal.

Generally, in order to provide for a pacing in the ventricle using an atrial tracking, a sensing of atrial activity is required to provide for detected atrial sense markers in order to time a pacing in the ventricle in atrioventricular (AV) synchrony.

Figure 4:
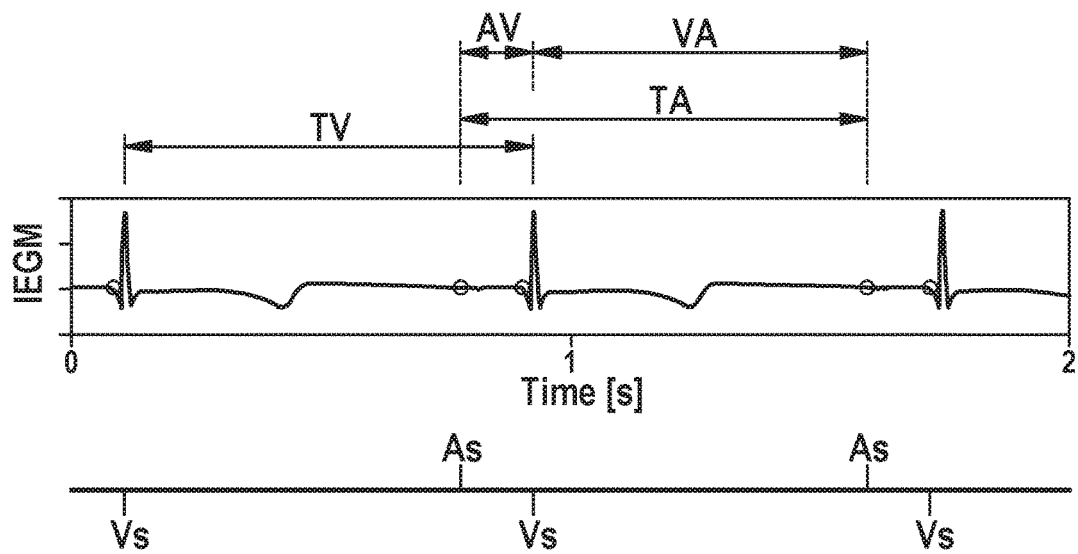
FIG. 4 is a graphical representation of an intra-cardiac electrogram (IEGM)

Referring now to FIG. 4, a sensing signal picked up by using the electrode configuration 11, 12, 13, for example by using the pair of electrodes 11 and 13 defining the far field vector A, an intra-cardiac electrogram IEGM is obtained and processed to derive atrial events As and ventricular events Vs, the atrial events As relating to a so-called P wave in the electrogram signal and the ventricular events Vs being derived from a so-called QRS wave form in the signal.

Generally, ventricular events Vs arise at a ventricular interval TV, and atrial events As arise at an atrial interval TA, wherein the ventricular interval TV and the atrial interval TA (approximately) match in case the ventricular rate is in synchrony with the atrial rate. A ventricular event Vs herein appears at a delay—the so-called atrioventricular delay AV—following a prior atrial event As, due to the fact that within the intrinsic conduction mechanism of the heart the atrium is caused to contract prior to the ventricle.

As visible from FIG. 4, the amplitude of a QRS waveform associated with a ventricular event Vs is much larger than the amplitude of a P wave associated with an atrial event As. Hence, the detection of an atrial event As requires a processing of the signal, involving for example a filtering, in particular a bandpass filtering, a rectification and/or a windowing in order to determine, for example by monitoring a threshold crossing, whether an atrial event As occurs.

Figure 5:
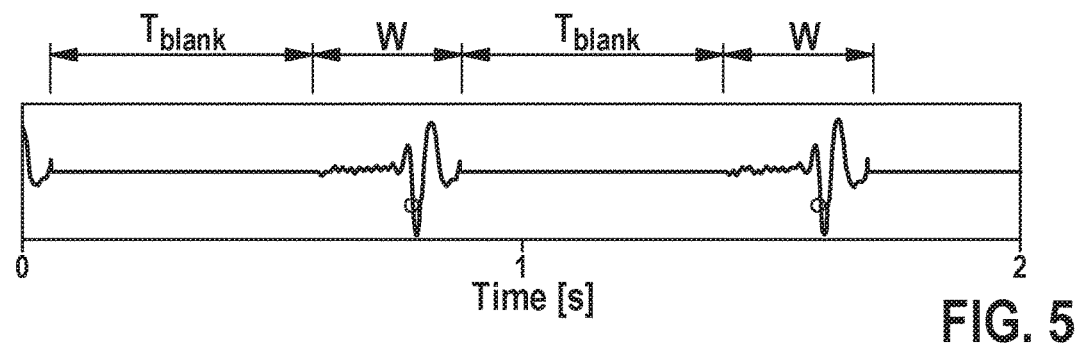
FIG. 5 is a graphical representation of a processed signal stream derived from the intra-cardiac electrogram to derive atrial events.

In one embodiment, as illustrated in FIG. 5, a windowed search strategy may be employed by using a search window W in which it is searched for an atrial event As. In particular, within a sense signal, for example an electrical sense signal, a search window W of a predefined width and predefined temporal position with respect to a prior ventricular event Vs may be used, the search window W being centered for example around a calculated ventricular-atrial delay VA as illustrated in FIG. 4.

The ventricular-atrial delay VA represents a time following a prior ventricular event Vs at which a next atrial event As is predicted to occur, the ventricular-atrial delay VA being computed for example from an average atrial interval TA and an average atrioventricular delay AV at which a ventricular pacing or sense event Vs has occurred after a prior atrial event As. According to the ventricular-atrial delay VA the temporal position of the window W is determined such that signal portions not relating to atrial activity, in particular a QRS waveform, are excluded from a signal processing, such that stronger amplitudes of signals relating to a heart activity other than an atrial activity are suppressed and do not interfere with a processing of atrial signals.

In particular, a search circuitry associated with a particular sensor configuration 11, 13, 16, 17, 18 may be active only during an associated search window W, but is switched off during a blanking window $T_{blank}$ as illustrated in FIG. 5, such that power is saved and only such signals are sensed which potentially relate to atrial activity.

Figure 6:
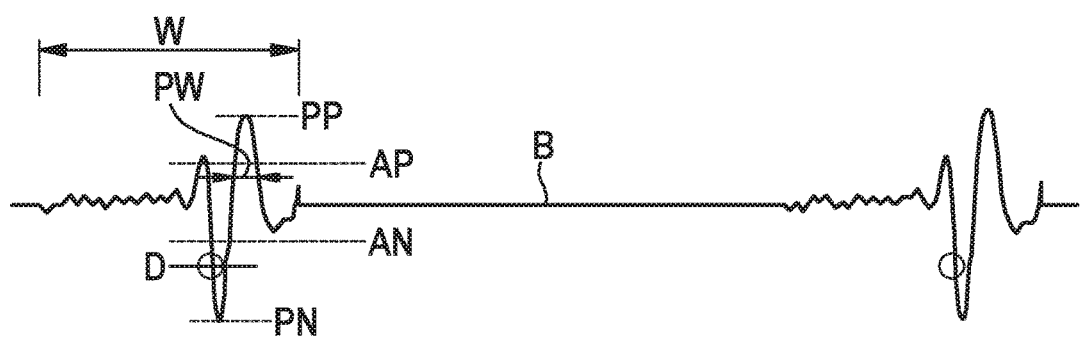
FIG. 6 is a graphical representation of a portion of the processed signal to determine characteristic values from that signal for the determination of an atrial event.

A signal sensed in this way may be processed as illustrated in FIG. 6. In particular, from a sense signal characteristic values characterizing an atrial event As may be derived, in particular a positive peak amplitude PP, a negative peak amplitude PN, a positive average value AP relating to an average of signal portions above a baseline B, and a negative average value AN relating to negative signal portions below the baseline B. In addition, for example a pulse width PW relating to the full-width-at-half-maximum of a peak in the signal may be determined. Alternatively or in addition a frequency analysis may be performed in order to determine an energy content of the signal in certain frequency bands.

In order to determine an atrial event, for example a threshold crossing of a threshold D may be monitored. Herein, for example a positive threshold and/or a negative threshold may be applied, wherein it may be found for an atrial event if either one or both of the thresholds are crossed by the signal. The thresholds herein may be adaptive and may be determined for example in dependence of other characteristic values, such as the negative peak amplitude PN or the positive peak amplitude PP.

Figure 7:
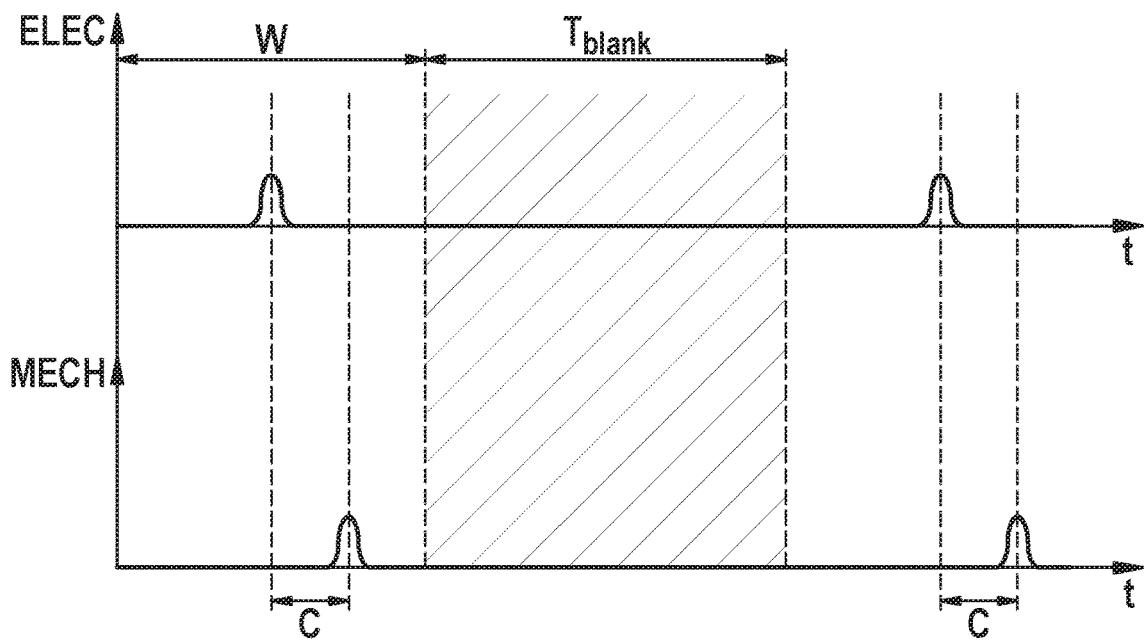
FIG. 7 is a graphical view of an electrical sense signal (top) and a mechanical sense signal (bottom) for detecting atrial events in a search window.

Referring now to FIG. 7, atrial contractions may cause signals in an electrical sense signal (top of FIG. 7) as well as in a mechanical sense signal (bottom of FIG. 7), for example relating to a pressure signal, a motion signal or a sound signal. Herein, a wave form relating to an atrial event in a mechanical signal (i.e., a signal received for example by using a pressure sensor, a motion sensor or a sound sensor) may occur at a delay C with respect to a wave form relating to an atrial event in an electrical signal, due to the different propagation mechanisms within the heart. In each case, though, a search window W is applied, and outside of the search window W, i.e., in a blanking window $T_{blank}$, the respective sense signal is switched off such that a detection for atrial events takes place only within the search window W.

Figure 8:
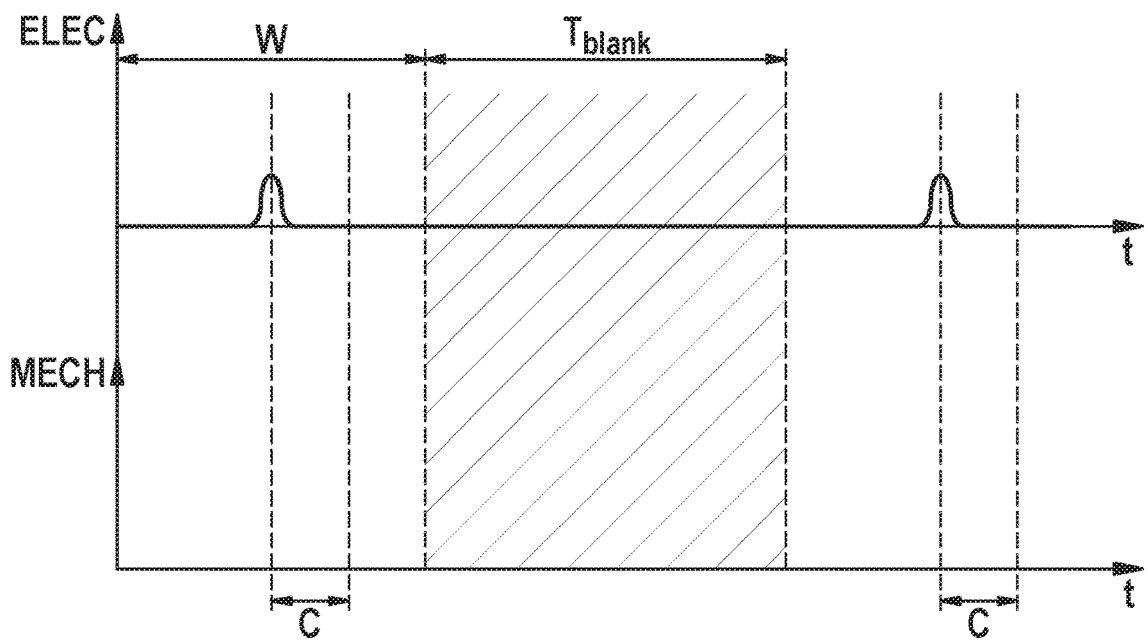
FIG. 8 is a graphical view in a sensing state in which only the electrical signal is used for sensing.
Figure 9:
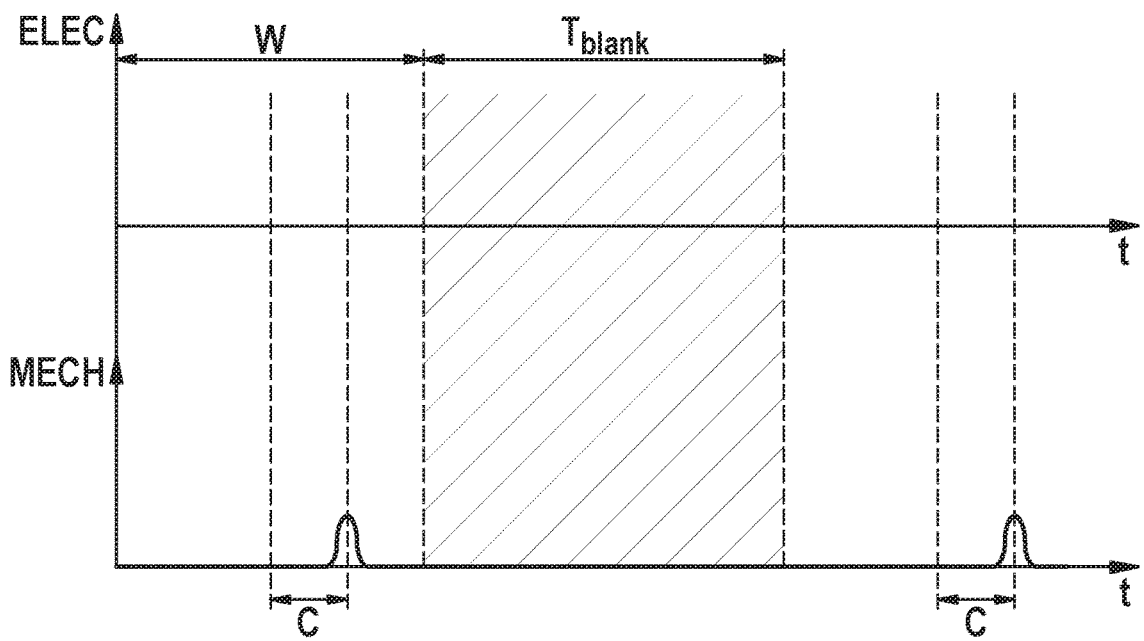
FIG. 9 is a graphical view in a sensing state in which only the mechanical signal is used for sensing.

Referring now to FIGS. 8 and 9, when only one sensor configuration is active, a sense signal is detected only using that sensor configuration. For example, FIG. 8 illustrates a sensing of an electrical signal only by using the electrode configuration, a sensing circuitry relating to other sensors, in particular mechanical sensors such as a motion sensor 16, a pressure sensor 17 and a sound sensor 18, are switched off. In FIG. 9, instead, a sensing circuitry relating to the electrode configuration for sensing an electrical signal is switched off, but a sensing circuitry relating to a mechanical sensor such as a motion sensor 16, a pressure sensor 17 and a sound sensor 18 is active for sensing a mechanical signal.

Figure 10:
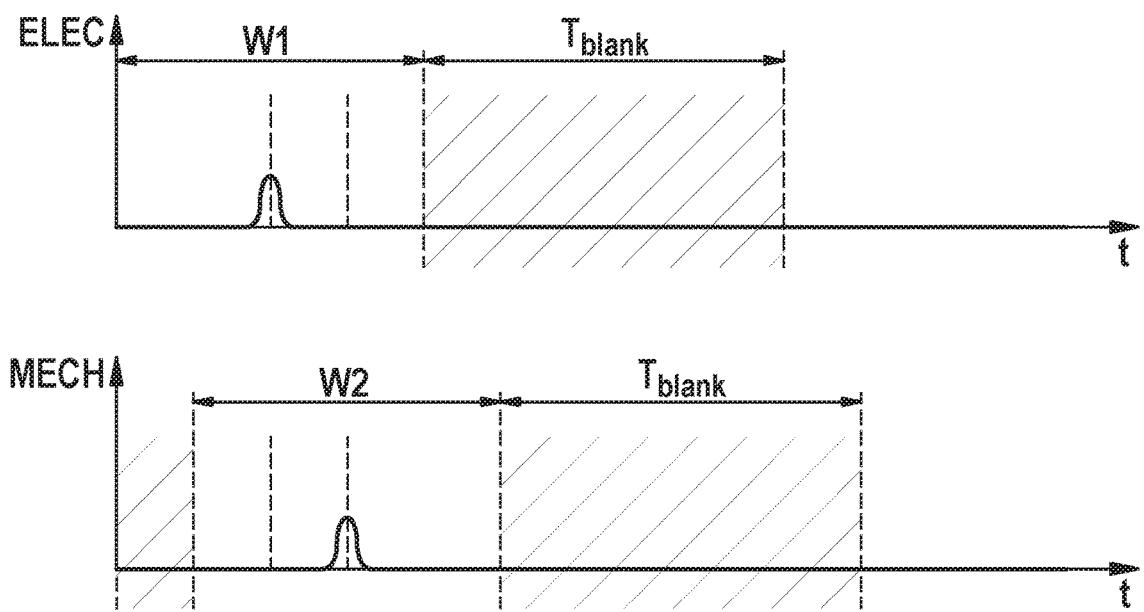
FIG. 10 is a graphical view illustrating different search windows to be applied for the electrical sense signal and the mechanical sense signal.

Referring now to FIG. 10, as the sense signals relating to the different sensor configurations may differ in their physical nature and may be delayed with respect to each other, also search windows W1, W2 for the different sensor signals may be defined differently. In particular, a search window W1 for an electrical sense signal may have a different temporal width and temporal position as compared to a search window W2 for a mechanical signal, such as a pressure signal, a motion signal or a sound signal.

Alternatively, the search windows W1, W2 may have an equal width and temporal position.

It herein is proposed to operate the processing circuitry 15 in different sensing states employing, in each sensing state, one of the sensor configurations 11, 13, 16, 17, 18 or a particular combination of the sensor configurations 11, 13, 16, 17, 18. In a first sensing state one of the sensor configurations 11, 13, 16, 17, 18 (or one combination of the sensor configurations 11, 13, 16, 17, 18) is used for sensing a signal and for deriving atrial events As from that signal, whereas the remaining sensor configurations 11, 13, 16, 17, 18 are switched off. When switching to another sensing state, instead, another sensor configuration 11, 13, 16, 17, 18 (or combination of sensor configurations 11, 13, 16, 17, 18) is used for deriving atrial events As.

One sensor configuration, for example the electrode configuration included of electrodes 11, 13 for detecting an atrial signal vector A or a motion sensor 16 including an accelerometer, may be defined as a primary sensor, wherein another sensor configuration may be defined as a secondary sensor. Hence, primarily the first, primary sensor configuration is used for sensing in a first sensing state, but in case a reliable detection of atrial events in the sense signal of the primary sensor configuration is no longer possible it is switched to the other, secondary sensor configuration to continue an atrial tracking in a second sensing state.

The switching from the first sensing state to the second sensing state may be controlled by the processing circuitry 15 according to one or multiple switching criteria.

For example, the processing circuitry 15 may evaluate, when in the first sensing state, whether an atrial event As can be identified in a search window W within a respective sense signal. If for a predetermined number of consecutive heart cycles no atrial event As can be identified, or if in a predefined percentage of a predetermined number of consecutive heart cycles no atrial event can be identified, the processing circuitry 15 may switch to the second sensing state in order to now sense for atrial events by using another sensor.

Alternatively or in addition, the processing circuitry 15 may analyze characteristic values of a sense signal in the first sensing state, for example in relation to a predefined threshold. For example, if a peak amplitude PN, PP comes close to a threshold, this may indicate that the signal amplitude is weak, which may cause a switch to the second sensing state.

Figure 11:
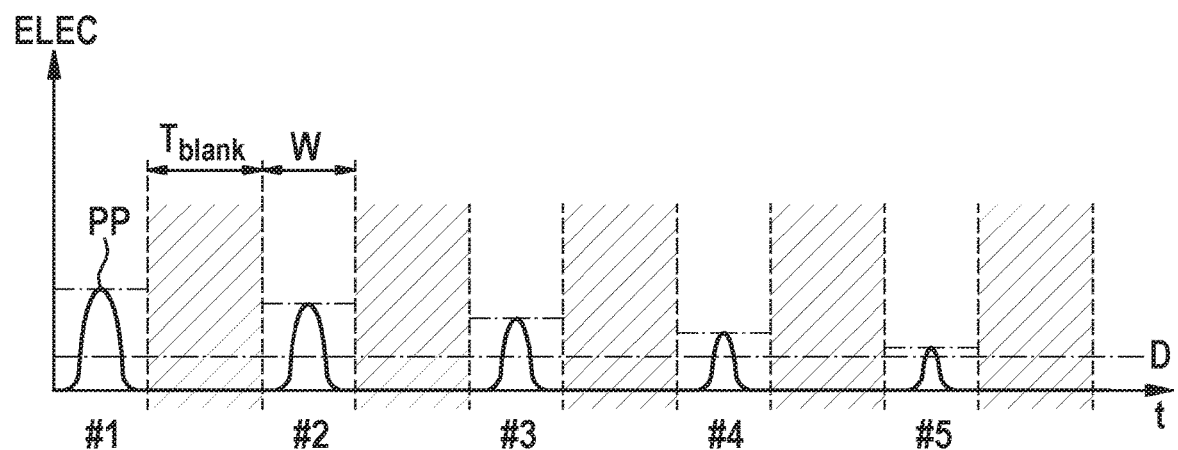
FIG. 11 is a graphical view of atrial events in a number of consecutive search windows relating to multiple heart cycles.

Alternatively or in addition, the processing circuitry 15 may analyze a trend of characteristic values over multiple heart cycles, as this is illustrated in FIG. 11. For example, a peak amplitude PN, PP may be observed over multiple heart cycles #1-#5, wherein a switching to a second sensing state may be caused if it is found that a trend indicates that the peak amplitude PN, PP progressively decays towards a threshold value D.

A switching triggered by an analysis of characteristic values rather than according to a missing of atrial events As may be beneficial in that a switching to another sensing state may be initiated already prior to losing any atrial events As. The switching hence may already occur while atrial events As are still detectable in the first sensing state, but the risk of losing future atrial events As is present.

In the second sensing state atrial events are identified and tracked using a different sensor employing a different sensing modality. In the second sensing state a processing similar to the first sensing state may take place to detect atrial events as well as to monitor whether a reliable atrial tracking based on the second sense signal in the second sensing state is possible.

When in the second sensing state, a sense signal of the first, primary sensor configuration may be monitored continuously or periodically. If it is found that the sensor signal of the primary sensor configuration is again adequate for deriving a reliable atrial rate, it may be switched back to the first sensing state, hence using a detection of atrial events based on a sense signal of the primary sensor configuration.

If, when in the second sensing state, it is found that also an atrial tracking based on the second sense signal is not reliably possible, the processing circuitry 15 may switch to an asynchronous pacing mode in which atrial tracking is disabled. The ventricular pacing rate in this case may be controlled according to for example a rate response mechanism in which the ventricular pacing rate is varied according to sensor readings being indicative of a physical state of the patient.

The processing circuitry 15 may be configured to switch back to a synchronous pacing mode if either an atrial tracking based on the first sense signal in the first sensing state or the second sense signal in the second sensing state becomes available and adequate for a pacing. For this, when in the asynchronous mode the processing circuitry 15 may enter into a search state for periodically searching for atrial events based on the first sense signal and the second sense signal. If no reliable, stable atrial rate can be derived from either the first sense signal or the second sense signal, the processing circuitry 15 remains in the asynchronous mode.

Figure 12:
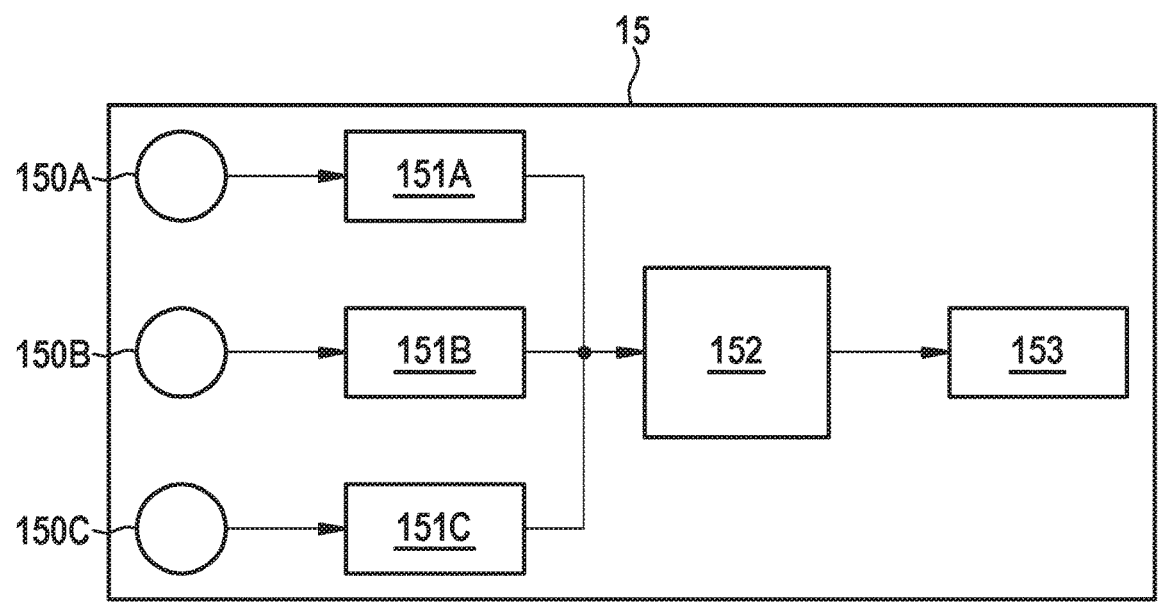
FIG. 12 is a block diagram of a processing circuitry for processing different sense signals.

Referring now to FIG. 12, the processing circuitry 15 may include different functional paths for analyzing different sense signals obtained from sensor inputs 150A, 150B, 150C, associated with different sensor configurations 11, 13, 16, 17, 18.

In particular, sensor inputs 150A, 150B, 150C may be provided to pre-processing units 151A, 151B, 151C for a pre-processing, wherein each sensor input 150A, 150B, 150C may undergo an individual preprocessing, for example to take account of a different timing in different sensor signals. In one embodiment, the pre-processing units 151A, 151B, 151C may perform a signal sampling and conversion. In another embodiment the preprocessing units 151A, 151B, 151C may perform, in addition to a sampling and conversion, an event detection such that in the preprocessing units 151A, 151B, 151C atrial events As are already identified.

An output of the preprocessing units 151A, 151B, 151C is forwarded to a processing unit 152 for performing a further processing, for example to perform an event detection, a noise detection, a correlation of information received from the different pre-processing units 151A, 151B, 151C, and an arrhythmia detection.

The processing unit 152 may, in one embodiment, also perform an analysis for the switching between different sensing states, and may trigger a switching from one sensing state to another.

An output of the processing unit 152 is fed to a timer unit 153 for the generation of pacing signals at a suitable timing in particular with respect to detected atrial events As.

In each sensing state a signal from a single sensor configuration 11, 13, 16, 17, 18 may be analyzed and processed to derive atrial events As, or a combination of signals from multiple sensor configurations 11, 13, 16, 17, 18 may be analyzed and processed. For example, in one sensing state an electrical sense signal from the pair of electrodes 11, 13 defining the far-field vector A may be received, processed and analyzed. In another sensing state signals from multiple mechanical sensors, for example a combination of signals from the motion sensor 16, the pressure sensor 17 and the sound sensor 18 of the embodiment of FIG. 3, may be processed and analyzed to detect atrial events As based on the combination of sense signal. For a combined analysis the signals may be correlated to each other, may be shifted in time with respect to each other to align the signals, and may be processed by applying a filtering, for example a low-pass filtering or a bandpass filtering, or a rectification or the like.

It will be apparent to those skilled in the art that numerous modifications and variations of the described examples and embodiments are possible in light of the above teaching. The disclosed examples and embodiments are presented for purposes of illustration only. Other alternate embodiments may include some or all of the features disclosed herein. Therefore, it is the intent to cover all such modifications and alternate embodiments as may come within the true scope of this invention.

LIST OF REFERENCE NUMERALS

1 Leadless pacemaker device
10 Housing
100 Tip
101 Far end
11 First electrode (pacing electrode)
12 Second electrode (pacing ring)
13 Third electrode
14 Fixation device
15 Processing circuitry
150A, B, C Sensor input
151A, B, C Pre-processing unit
152 Processing unit
153 Timing unit
16 Motion sensor
17 Pressure sensor
18 Sound sensor
A Atrial vector
AN Negative average
AP Positive average
As Atrial event
AV Atrial-ventricular delay
AVN Atrioventricular node
B Baseline
C Delay
D Threshold value
H HIS bundle
LA Left atrium
LBB Left bundle branch
LV Left ventricle
M Intra-cardiac tissue (myocardium)
P Pacing vector
PN Negative peak value
PP Positive peak value
PW Peak width
RA Right atrium
RBB Right bundle branch
RV Right ventricle
TA Atrial interval
TV Ventricular interval
$T_{blank}$ Blanking window
SAN Sinoatrial node
V Ventricular vector
VA Ventricular-atrial delay
Vs Ventricular event
W, W1, W2 Search window

The invention claimed is:

1. A leadless pacemaker device configured to provide for an intra-cardiac pacing, the leadless pacemaker device comprising:
a first sensor configuration configured to receive a first sense signal;
a second sensor configuration configured to receive a second sense signal, said second sensor configuration being a sound sensor;
a processing circuitry configured to generate ventricular pacing signals for stimulating ventricular activity at a ventricular pacing rate, said processing circuitry being configured to derive, in a first sensing state, atrial events from said first sense signal for controlling said ventricular pacing rate based on said atrial events, said processing circuitry being further configured to switch, based on at least one switching criterion, from said first sensing state to a second sensing state in which said processing circuitry is configured to derive atrial events from said second sense signal;
said processing circuitry further configured to perform an analysis, as a switching criterion, of at least one characteristic value derived from said first sense signal;
said processing circuitry configured to switch to said second sensing state based on said analysis of said at least one characteristic value, said analysis of said at least one characteristic value including analyzing a trend of said at least one characteristic value over a multiplicity of heart cycles, wherein said processing circuitry switches to said second sensing state if said analysis indicates a trend in which the characteristic value progressively decays towards a threshold over said multiplicity of heart cycles;
said second sense signal being received by said second sensor configuration for a detection of atrial events.

2. The leadless pacemaker device according to claim 1, wherein said first sensor configuration includes at least two electrodes for receiving an electrical sense signal indicative of an atrial activity.

3. The leadless pacemaker device according to claim 2, which further comprises a housing having a tip and a far end, one of said electrodes being disposed in a vicinity of said tip, another of said electrodes being disposed in a vicinity of said far end, and said electrical sense signal being received by using said electrode in the vicinity of said tip and said electrode in the vicinity of said far end.

4. The leadless pacemaker device according to claim 2, further comprising a third sensor configuration including at least a pressure sensor for sensing a pressure signal.

5. The leadless pacemaker device according to claim 2, further comprising a motion sensor configuration including an accelerometer configured to sense an acceleration along at least one spatial axis.

6. The leadless pacemaker device according to claim 1, wherein said processing circuitry is configured to detect, in said first sensing state, an atrial event from said first sense signal in a first search window having a predefined temporal position with respect to a ventricular event caused by a ventricular activity, and to detect, in said second sensing state, an atrial event from said second sense signal in a second search window having a predefined second temporal position with respect to a ventricular event caused by a ventricular activity.

7. The leadless pacemaker device according to claim 6, wherein said first search window and said second search window differ in at least one of a temporal width or a temporal position of said search windows.

8. The leadless pacemaker device according to claim 1, wherein said processing circuitry is configured to analyze, as a switching criterion, whether an atrial event is detectable in said first sense signal, and said processing circuitry is configured to switch to said second sensing state if atrial events are not detectable in at least a portion of a predetermined number of heart cycles.

9. The leadless pacemaker device according to claim 1, wherein said analysis of said at least one characteristic value includes analyzing at least one of a peak value, an average value, a peak width or a frequency content of said first sense signal.

10. The leadless pacemaker device according to claim 1, wherein said analysis of said at least one characteristic value includes analyzing whether said at least one characteristic value is within a predefined distance from a threshold value.

11. The leadless pacemaker device according to claim 1, wherein said processing circuitry is configured to switch from said second sensing state to said first sensing state upon detecting atrial events in said first sensing state being adequate for a pacing.

12. The leadless pacemaker device according to claim 1, wherein said processing circuitry is configured to switch to an asynchronous pacing mode in case atrial events being adequate for a pacing are not detectable in said first sensing state and said second sensing state.

13. A method for operating a leadless pacemaker device configured to provide for an intra-cardiac pacing, the method comprising the following steps:
   using a processing circuitry to generate ventricular pacing signals for stimulating ventricular activity at a ventricular pacing rate;
   using a first sensor configuration to receive a first sense signal;
   using the processing circuitry, in a first sensing state, to derive atrial events from the first sense signal for controlling the ventricular pacing rate based on the atrial events;
   using the processing circuitry, based on at least one switching criterion, to switch from the first sensing state to a second sensing state in which a second sense signal is received by a second sensor configuration being a sound sensor;
   using the processing circuitry to perform an analysis, as a switching criterion, of at least one characteristic value derived from the first sense signal;
   switching, with the processing circuitry, to the second sensing state based on the analysis of the at least one characteristic value, the analysis of the at least one characteristic value including analyzing a trend of the at least one characteristic value over a multiplicity of heart cycles, wherein the processing circuitry switches to the second sensing state if the analysis indicates a trend in which the characteristic value progressively decays towards a threshold over said multiplicity of heart cycles;
   using the processing circuitry to derive atrial events from the second sense signal in the second sensing state.

* * * * *